United States Patent [19]

Salinas

[11] Patent Number: 5,728,125
[45] Date of Patent: Mar. 17, 1998

[54] MENSTRUAL DETECTOR

[76] Inventor: Maria Teresa Echeverria Salinas, José Aguilar, 8 Puerta, 10-4 46022 Valencia, Spain

[21] Appl. No.: 531,645

[22] Filed: Sep. 21, 1995

[30] Foreign Application Priority Data

Sep. 27, 1994 [ES] Spain ................................ 9402454

[51] Int. Cl.$^6$ ........................................... A61F 13/16
[52] U.S. Cl. ........................................... 604/361
[58] Field of Search ........................ 604/358, 361, 604/385.1, 362; 602/2, 8, 14

[56] References Cited

U.S. PATENT DOCUMENTS

| | | | |
|---|---|---|---|
| 3,675,654 | 7/1972 | Baker et al. | 604/361 |
| 3,794,024 | 2/1974 | Kokx et al. | 604/361 |
| 4,959,060 | 9/1990 | Shimomura et al. | 604/368 |
| 5,178,139 | 1/1993 | Angelillo et al. | 604/358 |

*Primary Examiner*—John G. Weiss
*Assistant Examiner*—David J. Cho
*Attorney, Agent, or Firm*—Gary M. Nath; Suet M. Chong; Nath & Associates

[57] ABSTRACT

A menstrual detector comprising a sanitary napkin of reduced dimensions, formed by a thin layer of absorbent material, and within the interior of the absorbent material a small cavity containing a temperature-sensitive reactive chemical product that can respond by turning cold when it comes into contact with and dissolves in a menstrual flow.

13 Claims, 1 Drawing Sheet

MENSTRUAL DETECTOR

TECHNICAL FIELD

This invention relates to a menstrual detector that discreetly warns the user of the arrival of her period.

BACKGROUND OF THE INVENTION

One of the most common feminine hygiene products for controlling menstruation is the sanitary napkin. The appropriate time to use a sanitary napkin is difficult to determine, however, because of the irregularities that often attend menstrual cycles and, especially, the unpredictability of the precise moment that the flow will begin.

Although women have attempted to calculate the arrival of her period by observing her physical symptoms, such efforts are tedious and the estimates may nevertheless be wrong. In the absence of any reliable means of predicting its onset, the period frequently arrives without the woman having taken the proper precautions, with the result of annoying and embarrassing stains on her clothes.

As a precautionary measure, a woman may use a smaller sanitary napkin days before she thinks that her period will arrive. In any case, she must be very watchful and, unfortunately, even so she cannot avoid the occasional flow leaking through to the skirt, pants, etc. Such risk increases for women who must be on their feet many hours, as is the case of teachers, shop assistants, nurses, etc.

SUMMARY OF THE INVENTION

To provide a practical preventive solution for these drawbacks, a menstrual detector is proposed according to this invention.

The proposed detector basically comprises a sanitary napkin of reduced dimensions, formed by a thin layer of absorbent material, and within the absorbent material, a small cavity filled with a product, such as sodium thiosulfate or sodium hyposulfite, which can react to the temperature of the menstrual flow by turning cold upon coming into contact with and dissolving in the warm menstrual flow.

The cavity that contains the reactive product can extend as a thin layer throughout the interior of the absorbent material, or partially in only one area located anywhere in the absorbent material. Preferably, the cavity is situated in the central area of the absorbent material.

In this manner a completely effective detector is obtained, which, simply by producing a cold sensation, allows the user to be warned with total discretion of the arrival of her menstrual flow, so that she can take the proper precautions with sanitary napkins capable of greater absorption.

The reduced mass of material with which it is made makes the menstrual detector very inexpensive and easy to use. Furthermore, the detector is absolutely inoffensive, since the reactive material included inside is completely innocuous.

Because of all of the above reasons, the proposed detector is very useful for its intended purpose.

DETAILED DESCRIPTION OF THE INVENTION

Figure 1:
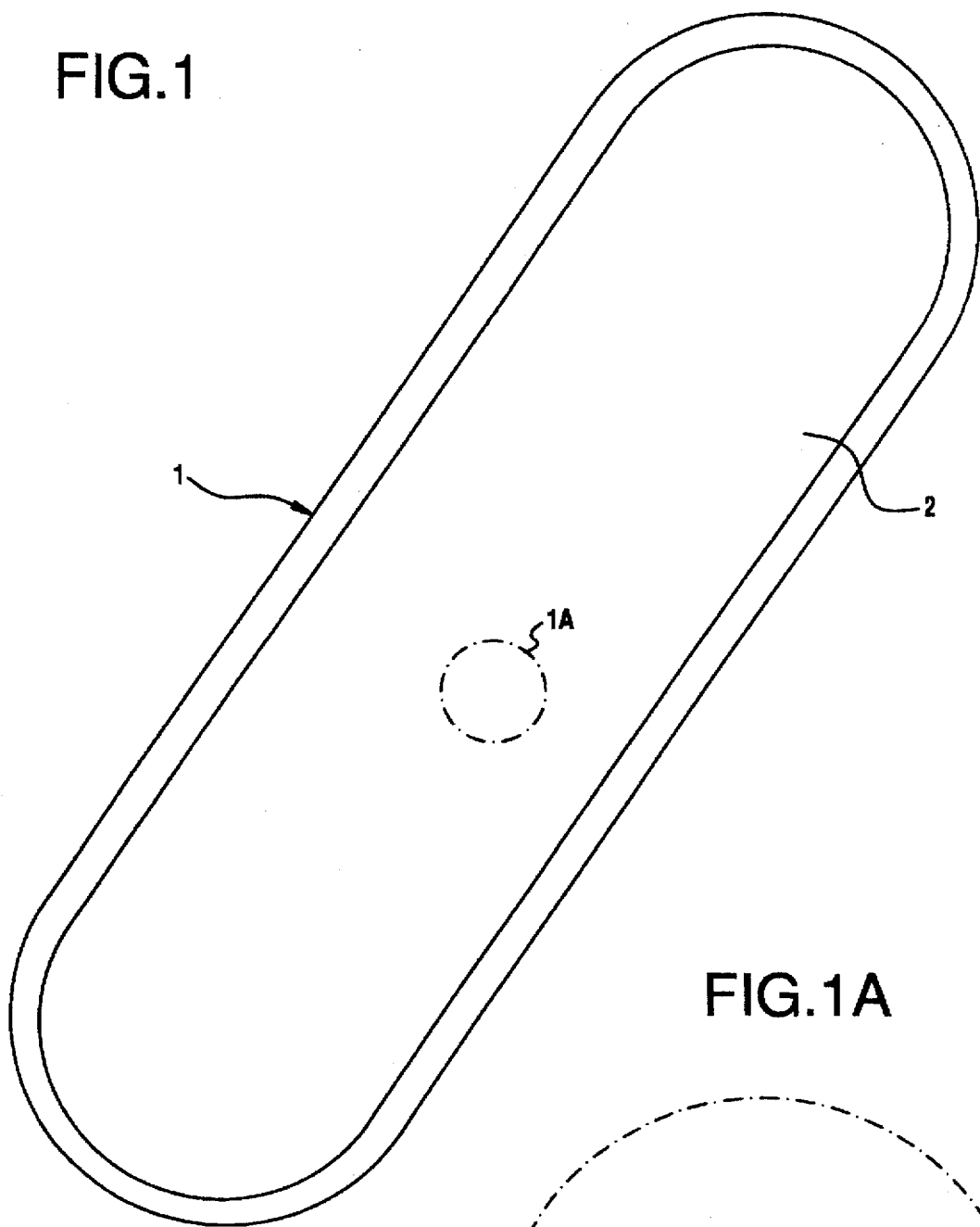
FIG. 1 provides a perspective and a magnified cross-sectional view of a menstrual detector according to this invention.
Figure 1A:
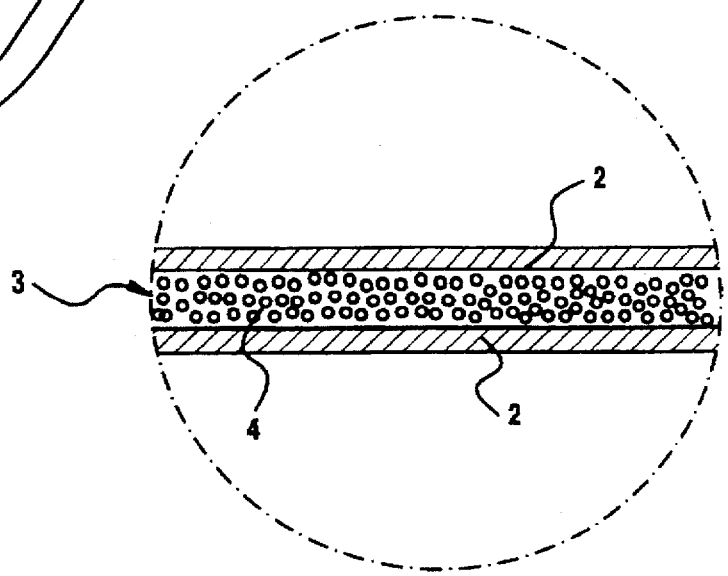

To better understand the nature of this invention, in the attached drawings we show, by way of a merely illustrative, nonlimiting example, a preferred commercial application, to which we refer in our description. In the drawings:

FIG. 1 represents a perspective of the proposed detector, according to a nonlimiting example, with a magnified cross-sectional view of the area housing the internal reactive product.

The subject of the invention relates to a menstrual detector, intended to be used before menstruation to discreetly alert the user the moment her menstrual flow begins, so she may take the proper precautions to avoid the disagreeable and embarrassing situation of leakage through her clothes.

The proposed detector comprises a sanitary napkin of little thickness (1), formed by a thin layer of absorbent material (2), within whose interior a small cavity (3) is included and filled with a product (4) with specific reactive characteristics.

This product (4) preferably comprises sodium thiosulfate or sodium hyposulfite, which can respond by turning cold upon coming into contact with and dissolving in a hot liquid, such as a menstrual flow.

The sanitary napkin (1) can adopt any conventional shape or form, the only particularity being the reduced thickness of the absorbent material (2), so that its use will provide little discomfort.

The reduced thickness makes the sanitary napkin (1) optimally suited for use during the premenstrual period because the user can achieve secure protection against small flows with little discomfort. When the menstrual flow arrives, it dissolves product (4) contained in the internal cavity (3). The product (4) reacts by producing a cold sensation, so that the user becomes aware of the situation in an intimate and totally discrete manner, and can adopt appropriate measures to avoid embarrassing leakage by using more absorbent sanitary napkins.

Thus, sanitary napkin (1) is perfectly tailored to be used as a hygienic and protective shield during the premenstrual cycle, with the purpose of avoiding embarrassing situations. It is especially ideal for use on trips and in certain jobs which require standing and facing an audience, such as, for example, schoolteaching, etc.

The cavity (3) that contains the reactive product (4) can extend as a thin layer throughout the interior of the sanitary napkin (1), or partially in only one area located anywhere in the sanitary napkin (1). Preferably, the cavity (3) is situated in the central area, since this where the flow first arrives and, hence, where its presence can be most rapidly detected. In any case, the presence of reactive product (4) will not be harmful to the user, since the substance employed is totally innocuous.

The nature of this invention being thus described, it will be obvious that the same may be varied in many ways. For instance, changes in the shape, material and structure may be introduced into the whole or constituent parts of the menstrual detector. Such modifications are not to be regarded as a departure from the spirit and scope of the invention and all such modifications are intended to be included within the scope of the following claims.

I claim:

1. A premenstrual early warning detector comprising a sanitary napkin of reduced dimensions, formed by a thin layer of an absorbent material without a liquid impermeable back sheet, said absorbent material having an interior, and within the interior of the absorbent material a temperature-sensitive reactive chemical product that can respond by turning cold when it comes into contact with and dissolves in a menstrual flow, said chemical product located sufficiently near a surface of the absorbent material where the menstrual flow first arrives such that the detector will alert a user the moment the menstrual flow begins.

2. The premenstrual early warning detector of claim 1, wherein the reactive product consists essentially of sodium thiosulfate or sodium hyposulfite.

3. The premenstrual early warning menstrual detector of claim 2, wherein the reactive product employed consist essentially of sodium thiosulfate.

4. The premenstrual early warning menstrual detector of claim 2, wherein the reactive product employed consist essentially of sodium hyposulfite.

5. The premenstrual early warning menstrual detector of claim 4, wherein the cavity containing the reactive product extends as a thin layer throughout the interior of the absorbent material.

6. The premenstrual early warning menstrual detector of claim 5, wherein the cavity affects only a partial area of the absorbent material.

7. The premenstrual early warning detector of claim 6, wherein the cavity is located in a central area of the absorbent material.

8. The premenstrual early warning menstrual detector of claim 1, wherein the temperature-sensitive reactive chemical product is in a small cavity within the interior of the absorbent material.

9. The premenstrual early warning menstrual detector of claim 8, wherein the cavity containing the reactive product extends as a thin layer throughout the interior of the absorbent material.

10. The premenstrual early warning menstrual detector of claim 9, wherein the cavity affects only a partial area of the absorbent material.

11. The premenstrual early warning menstrual detector of claim 10, wherein the cavity is located in a central area of the absorbent material.

12. The premenstrual early warning detector of claim 8, wherein the reactive product consists essentially of sodium thiosulfate or sodium hyposulfite.

13. The premenstrual early warning detector of claim 1, which enables the user to detect the amount of the menstrual flow based on the intensity of the cold sensation.

* * * * *

UNITED STATES PATENT AND TRADEMARK OFFICE
CERTIFICATE OF CORRECTION

PATENT NO. : 5,728,125
DATED : March 17, 1998
INVENTOR(S) : Maria Teresa ECHEVERRIA SALINAS It is certified that error appears in the above-identified patent and that said Letters Patent is hereby corrected as shown below:

Claim 3, column 3, line 9, "consist" should read as "consists";
Claim 4, column 3, line 12, "consist" should read as "consists";

Claim 5 should depend upon claim 12, and claims 5-12 should be renumbered as follows in order that claims 5-7 follow claim 12:

Claim 5, column 3, should be renumbered as claim "10", which depends upon "claim 9";
Claim 6, column 3, should be renumbered as claim "11", which depends upon "claim 10";
Claim 7, column 3, should be renumbered as claim "12", which depends upon "claim 11".
Claim 8, column 4, should be renumbered as claim "5";
Claim 9, column 4, should be renumbered as claim "6", which depends upon "claim 5";
Claim 10, column 4, should be renumbered as claim "7", which depends upon "claim 6";
Claim 11, column 4, should be renumbered as claim "8", which depends upon "claim 7"; and

UNITED STATES PATENT AND TRADEMARK OFFICE
CERTIFICATE OF CORRECTION

PATENT NO. : 5,728,125
DATED : March 17, 1998
INVENTOR(S) : Maria Teresa ECHEVERRIA SALINAS It is certified that error appears in the above-indentified patent and that said Letters Patent is hereby corrected as shown below:

Claim 12, column 4, should be renumbered as claim "9", which depends upon "claim 5".

Signed and Sealed this

Twenty-eighth Day of July, 1998

Attest:

BRUCE LEHMAN

Attesting Officer    Commissioner of Patents and Trademarks